(12) United States Patent
aWengen et al.

(10) Patent No.: US 7,628,812 B2
(45) Date of Patent: Dec. 8, 2009

(54) OSSICLE PROSTHESIS

(75) Inventors: Daniel Felix aWengen, Binningen (CH); Uwe Steinhardt, Hirrlingen (DE)

(73) Assignee: Heinz Kurz GmbH Medizintechnik, Dusslingen (DE)

( * ) Notice: Subject to any disclaimer, the term of this patent is extended or adjusted under 35 U.S.C. 154(b) by 317 days.

(21) Appl. No.: 11/487,619

(22) Filed: Jul. 17, 2006

(65) Prior Publication Data
US 2007/0021833 A1 Jan. 25, 2007

(30) Foreign Application Priority Data
Jul. 21, 2005 (DE) .................. 20 2005 011 485 U
Feb. 11, 2006 (DE) .................. 20 2006 002 196 U

(51) Int. Cl.
*A61F 2/18* (2006.01)
*H04R 25/00* (2006.01)

(52) U.S. Cl. .......................................... 623/10; 600/25

(58) Field of Classification Search .................. 623/10; 606/151, 153, 157; 600/25; *A61F 2/18*
See application file for complete search history.

(56) References Cited

U.S. PATENT DOCUMENTS

| 5,935,167 | A | 8/1999 | aWengen | |
| 6,168,625 | B1 * | 1/2001 | Prescott | 623/10 |
| 6,862,805 | B1 * | 3/2005 | Kuzma et al. | 29/858 |
| 7,074,222 | B2 * | 7/2006 | Westerkull | 606/312 |
| 2002/0045939 | A1 | 4/2002 | Kurz | |
| 2002/0095063 | A1 * | 7/2002 | Kroll et al. | 600/25 |
| 2003/0130734 | A1 | 7/2003 | Antonelli et al. | |
| 2004/0064183 | A1 | 4/2004 | aWengen et al. | |

FOREIGN PATENT DOCUMENTS

| DE | 296 09 687 | 10/1996 |
| DE | 202 12 771 | 11/2002 |
| DE | 20 2004 001 008 | 4/2004 |
| DE | 20 2005 011 485 | 9/2005 |
| EP | 1 073 313 | 1/2001 |
| EP | 1 181 907 | 2/2002 |

* cited by examiner

*Primary Examiner*—Thomas J Sweet
*Assistant Examiner*—Yashita Sharma
(74) *Attorney, Agent, or Firm*—Michael J. Striker

(57) ABSTRACT

An ossicle prosthesis (10), which replaces or spans at least one member of the human ossicle chain; the ossicle prosthesis (10) has a securing element embodied as a first elastic clip (11), for mechanical connection with a member of the ossicle chain, the securing element is open towards the outside on one side, with an outer opening (14) for receiving the ossicle member. The securing element form-lockingly embraces the ossicle member with two regions which are joined together on their ends located diametrically opposite the outer opening (14) via a portion extending at a spacing from the ossicle member. The portion connecting the two regions has at least two circular recesses (19a, 19b), which are curved outward in a circular arc from the member of the ossicle chain.

20 Claims, 4 Drawing Sheets

OSSICLE PROSTHESIS

BACKGROUND OF THE INVENTION

The invention relates to an ossicle prosthesis which replaces or spans at least one member of the human ossicle chain, in which the ossicle prosthesis, on at least one end, has a securing element, embodied as a first elastic clip, for mechanical connection with a member of the ossicle chain, which element is designed in the form of a clamp, open toward the outside on one side, with an outer opening for receiving this member, with which the mechanical connection is to be made, and in which the clamp after the implantation of the prosthesis form-lockingly embraces this member with two regions which are joined together, on their ends located diametrically opposite the outer opening, via a portion extending at a spacing from this member.

A prosthesis of this kind that spans the stapes has already been described in German Utility Model DE 202 12 771 U1 of the present Applicant.

Ossicle prostheses are used, when the ossicles of the human middle ear are entirely or partly absent or damaged, to transmit the sound from the eardrum to the inner ear. The ossicle prosthesis has two ends, and depending on the specific given conditions, one end of their ossicle prosthesis is secured, for instance by means of a head plate, to the extension of the incus in the human ossicle chain, and the other end of the ossicle prosthesis is secured for instance to the stapes of the human ossicle chain, or is plunged directly into the inner ear. Often with the known ossicle prostheses, conducting sound between the eardrum and the inner ear is made possible only to a limited extent, since these prostheses are only extremely limitedly capable of replacing the natural anatomical features of the ossicle chain.

An ossicle prosthesis, known from German Utility Model DE 296 09 687 U1 of the present Applicant, which is a "predecessor" model of the prosthesis described in DE 202 12 771 U1, is distinguished in that it can be relatively easily implanted by simply being clipped on the long process of the incus. It holds solely by the clamping action of the clip. No further securing means are necessary.

Nevertheless, in the course of implantation, tilting of the prosthesis can occur, which would make the operation more difficult for the surgeon. To overcome this problem, in the ossicle prosthesis known from DE 202 12 771 U1 first cited above, the clamp is lengthened with at least one of its legs, which protrudes past the opening outward in the form of an arc, with which the prosthesis can be suspended, before being slipped on, from the long process of the incus of the human middle ear. By thus suspending the prosthesis from the long process of the incus, the surgeon gains the capability of changing the surgical instruments and for instance using a small hook for slipping the prosthesis onto the long process of the incus.

SUMMARY OF THE INVENTION

By comparison, the object of the present invention is now to design the stapes prosthesis known from DE 202 12 771 U1, using the simplest possible means, in such a way that its implantation in the middle ear is simplified still further.

This object is attained according to the invention with an ossicle prosthesis of the type defined at the outset, by providing that the portion connecting the two regions has at least two circular recesses, which are curved outward in a circular arc from the member of the ossicle chain with which member the mechanical connection is to be made. In this way, without major technical effort and in a simple way, the advantages of the above-described, known ossicle prosthesis of DE 202 12 771 U1, which defines the generic type, can be made use of, yet the spring characteristic of the structure can be designed as considerably "softer", which results in substantially improved manipulation of the ossicle prosthesis of the invention.

An especially preferred embodiment of the ossicle prosthesis of the invention is distinguished in that the securing element is embodied as double-walled, and its outer wall, on its side diametrically opposite the outer opening, is embodied as closed; and that the inner wall of the double-walled securing element is embodied as open on its side diametrically opposite the outer opening and has an inner opening to the adjacent outer wall. By the provision of an inner opening in the double-walled clip, the securing element of the ossicle prosthesis of the invention gains increased elasticity, so that compared with single-walled versions, an only minimal securing force lends a secure hold, and this force remains virtually constant even in the event of larger diameters of the ossicle that are for instance dictated anatomically. In particular the vessels extending laterally along the ossicle (for instance on the process of the incus) are not impaired or even interrupted by the clip, since the outer opening and the inner opening of the pig are positioned precisely on the lateral sides.

In a geometrically especially preferred refinement of this embodiment, the two end portions, separated by the inner opening and located diametrically opposite one another, of the inner wall each have a shape that is recessed in the direction of the outer wall adjacent to them and together form a receiving region for receiving the member of the ossicle chain with which the mechanical connection is to be made. With this shaping, both gentle and yet secure fastening of the prosthesis to the applicable ossicle can be optimally accomplished.

In practice, variations of this refinement have proven themselves in which the spacing between the inner opening and the portion, diametrically opposite it, of the outer wall is greater, preferably from two to ten times greater, than the spacing between the recessed end portions of the inner wall and the portion adjacent to each of them of the outer wall.

Other refinements of the above-described embodiment are distinguished in that an eye, nipple, or recess of the outer wall is provided in an outward-oriented region adjacent to the inner opening, which offers a possible way of suspending, catching or engagement with in particular a surgical instrument.

A refinement in which the inner wall, in the region of the outer opening, has a suspension recess is also advantageous; this makes it easier to apply the prosthesis in the middle ear.

In a further preferred refinement, the inner wall, in the region of the outer opening, has a lead-in chamfer, which likewise serves to make it easier to strip the securing element of the prosthesis over the applicable ossicle.

An embodiment of the invention in which the clamp with at least one of its legs is lengthened outward past its outer opening, and this lengthening has the form of an arc with which the prosthesis, before the clamp is slipped on, can be suspended from the member of the ossicle chain with which the mechanical connection is to be made, is very particularly preferred. The additional characteristics of this embodiment and their advantages have already been described in DE 202 12 771 U1 that defines the generic type here.

A further improved embodiment of the ossicle prosthesis of the invention provides that the clamp is provided on its outside with a nipple and/or a notch for slipping the prosthesis onto the member of the ossicle chain with which the mechanical connection is to be made. Thus manipulating the prosthesis can be made still easier, since the surgeon can engage this nipple with forceps or a hook. Instead of a nipple, the clamp can also be provided, on its side diametrically opposite the opening, with a notch for slipping the prosthesis onto the long process of the incus. An appropriate instrument can be positioned against this notch as well.

Further advantages are obtained if the clip does not completely embrace the applicable ossicle, such as the long process of the incus. As a result, the development of constrictions and hence the occurrence of potential necroses can be averted. It is especially advantageous if after the implantation the clip is located on the long ossicle in such a way that it does not rest on it in two regions of the circumference of the ossicle. The supply vessels on the ossicle are therefore touched only in the contacting regions. The other vessels extend in the two regions in which the clamp does not rest on the ossicle, so that the supply of nutrition to the ossicle, such as the long process of the incus and the process lenticularis, is not threatened.

Once the prosthesis of the invention has been surgically placed in the middle ear and the eardrum has been closed again, the so-called healing phase begins. In this period, scars form, and they engender unpredictable forces which can cause the prosthesis to shift out of its local position. For this reason, it is very helpful if the prosthesis can postoperatively automatically adapt to an altered position in the middle ear. Since given anatomical conditions of the ear, such as the location, form and size of the stapes, incus, malleus and the eardrum vary individually, it is generally highly advantageous if ossicle prostheses are not embodied rigidly but instead have a certain flexibility or variability. To attain this flexibility or variability, various securing and coupling devices for ossicles are known that have elastic parts and/or joints. One such articulated connection between a securing element that can be mounted on the base of the stapes and an elongated shaft of the ossicle prosthesis is described per se in European Patent Disclosure EP 1 181 907 B1 and is offered by the present Applicant under the tradename "Ball-Joint-Prothese". In an especially preferred embodiment of the ossicle prosthesis of the invention, the securing element is therefore located on one end of an elongated shaft that connects it to the other end of the prosthesis, and at least one ball joint is provided on or in the elongated shaft.

Besides postoperative position shifting, still another problem arises after the implantation of ossicle prostheses: The middle ear of the human body is in fact a "half-open bearing". Any implantation material that is introduced into the body in the context of reconstruction of the middle ear and its structures experiences a special stress as a result of the fact that a contaminated and infected environment, which as a rule attacks the material, prevails. Since the goal of implanting an ossicle prosthesis must always be the longest possible dwell time, without complications, of the implant in the middle ear of the patient, a long-lasting attack on the material can lead to damage of the prosthesis and/or to local infection. Neither of these consequences is tolerable. To lastingly prevent damage to both the implantation material and the surrounding tissue, in a further especially preferred embodiment of the invention, the surface of the ossicle prosthesis is coated either entirely or at least in some portions with a biologically active coating, and in particular a growth-inhibiting and/or growth-promoting and/or an antibacterial coating.

The ossicle prosthesis of the invention itself or parts thereof may be made of titanium and/or steel and/or tantalum and/or an alloy of the aforementioned metals. In particular, titanium as a material, besides its strength and excellent sound conduction properties, is also known to have excellent biocompatibility with the human middle ear.

Embodiments of the invention in which the prosthesis or parts thereof are made of a material with shape memory (=memory effect) or super-elastic properties, in particular of Nitinol, are advantageous with a view to the aforementioned postoperative positional adaptation.

However, embodiments of the invention are also possible in which the prosthesis or parts thereof are made of biocompatible plastics, in particular silicone, or fiber composite materials. With these materials, postoperative rejection reactions can also be prevented in most cases.

An embodiment of the device of the invention is especially preferred in which the mass distribution of the individual parts of the prosthesis is calculated as a function of a desired, predeterminable frequency response of the conduction of sound in the middle ear. Thus without major additional technical effort or expense, tuning of the sound propagation properties can be attained to a certain extent by means of an individually designed ossicle prosthesis.

Such a tuning effect can be attained in special embodiments, for instance by providing that as a function of a desired, predeterminable frequency response of the conduction of sound in the middle ear, at least one additional mass is secured to a part of the ossicle chain or of the prosthesis.

In advantageous refinements of these embodiments, the additional mass is secured to a part of the ossicle chain or of the prosthesis by means of a clip. Moreover, the additional mass and/or the clip can likewise be coated with a biologically active coating.

A further embodiment of the invention is distinguished in that the prosthesis is connected to an active vibrating part of an active, in particular implantable, hearing aid. Thus by using modern electronics, even extensive hearing damage can be overcome over wide ranges, or at least ameliorated substantially in its effects, and a physical connection of the prosthesis to the outside world based on the above-described coating in turn causes no problems from increased introduction of bacteria into the area of the middle ear, if the coating is suitably designed as antibacterial.

Depending on the individual defect to be eliminated in a patient by using the ossicle prosthesis of the invention, or at least ameliorated in its effects, the construction of the prosthesis is designed accordingly. In many embodiments, the prosthesis can for instance be secured on one side to the process of the incus and on the other to the stapes, or it can be immersed directly into the inner ear. In other further features of the invention, the prosthesis is secured on one side to the manubrium mallei and on the other to the incus or to the stapes, or is immersed directly into the inner ear. In this connection, a design in which the ossicle prosthesis is located at the end point of the malleus (the umbo) or directly next to it is advantageous; as a result, the maximum lever action is attained for mechanically transmitting sound through motions in the artificial or natural ossicle chain. Embodiments of the device of the invention that are also especially preferred are distinguished in that the ossicle prosthesis is coupled directly to the inner ear on one end, in particular via a piston, by means of opening the human cochlea (cochleotomy) of the elongated shaft.

In alternative embodiments of the ossicle prosthesis of the invention, located on the other end of the prosthesis, placed counter to the first clip, may be a further securing element, in particular embodied as a second clip and preferably double-walled, for mechanical connection to a further member of the ossicle chain.

Further characteristics and advantages of the invention will become apparent from the ensuing detailed description of exemplary embodiments of the invention in conjunction with the drawing figures, which show details essential to the invention, and from the claims. The individual characteristics can each be realized individually or a plurality of them in arbitrary combinations in variations of the invention can be attained.

In the schematic drawing, exemplary embodiments of the invention are shown, which are explained in further detail in the ensuing description.

DESCRIPTION OF THE PREFERRED EMBODIMENTS

Figure 1:
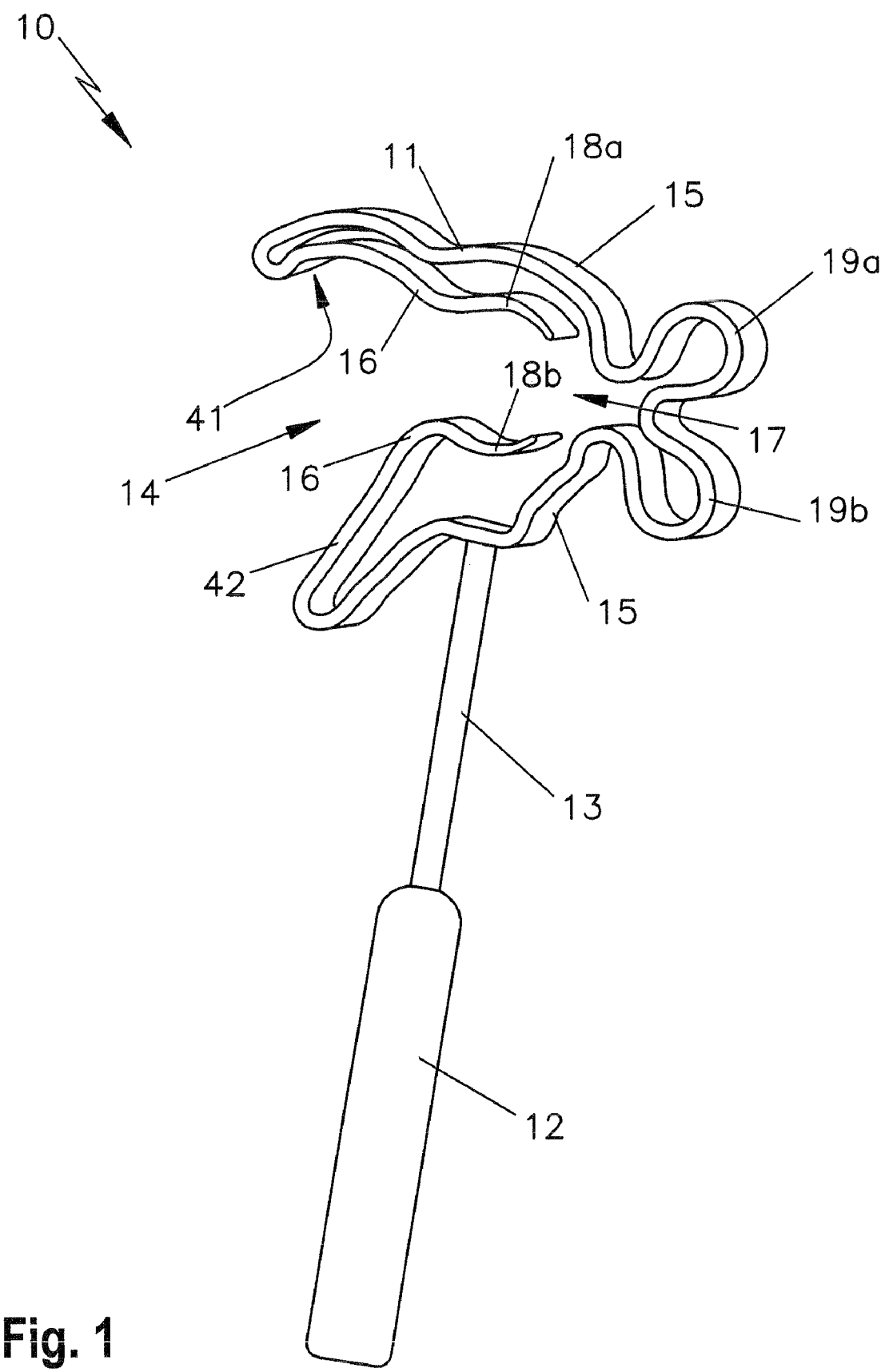
FIG. 1, a schematic three-dimensional view of one embodiment according to the invention, with a double-walled clip as the first securing element on an elongated shaft and with a piston on the other end of the shaft.

FIG. 1 schematically shows an ossicle prosthesis 10, which on one end is secured to a member of the ossicle chain in the middle ear, for instance to the manubrium mallei in the vicinity of the umbo, where the malleus has mechanical contact with the eardrum, or for instance on the process of the incus. On its other end, the ossicle prosthesis 10 changes into a piston 12, which protrudes into the inner ear through an opening (not shown in the drawing) in the base of the stapes. As an acoustically nonabsorbing connecting member between the first clip 11 and the piston 12, an elongated shaft 13 is provided.

The clip 11 in the exemplary embodiment shown is embodied as double-walled, in the form of a clamp open to the outside on one side, with an outer opening 14 for receiving the member of the ossicle chain with which the mechanical connection is to be made. The outer wall 15 of the double-walled securing element is closed on its side diametrically opposite the outer opening 14, and the inner wall 16 on its side located diametrically opposite the outer opening 14 is embodied as open and has an inner opening 17 to the adjacent outer wall 15. The two end portions 18a, 18b, diametrically one another and separated by the inner opening 17, of the inner wall 16 each have a shape that is recessed in the direction of the outer wall 15 adjacent to them and together form a receiving region for receiving the member of the ossicle chain with which the mechanical connection is to be made.

After the implantation of the prosthesis 10 in the middle ear, the clamp embraces this member in form-locking fashion by two regions (in FIG. 1, the end portions 18a, 18b), which are joined together on their ends, diametrically opposite the outer opening 14, via a portion (in the embodiment shown in FIG. 1, the outer wall 15) that extends spaced apart from this member. This portion joining the two regions has at least two (and in FIG. 1, precisely two) circular recesses 19a, 19b, which in order to lend the elastic clip 11a softer spring characteristic are curved in a circular arc outward by the member of the ossicle chain with which the mechanical connection is to be made.

In the embodiment shown in FIG. 1, the clip 11 is designed such that the inner wall 16, in the region of the outer opening 14, has a suspension recess 41 and a lead-in chamfer 42 as aids in application.

Figure 2A:
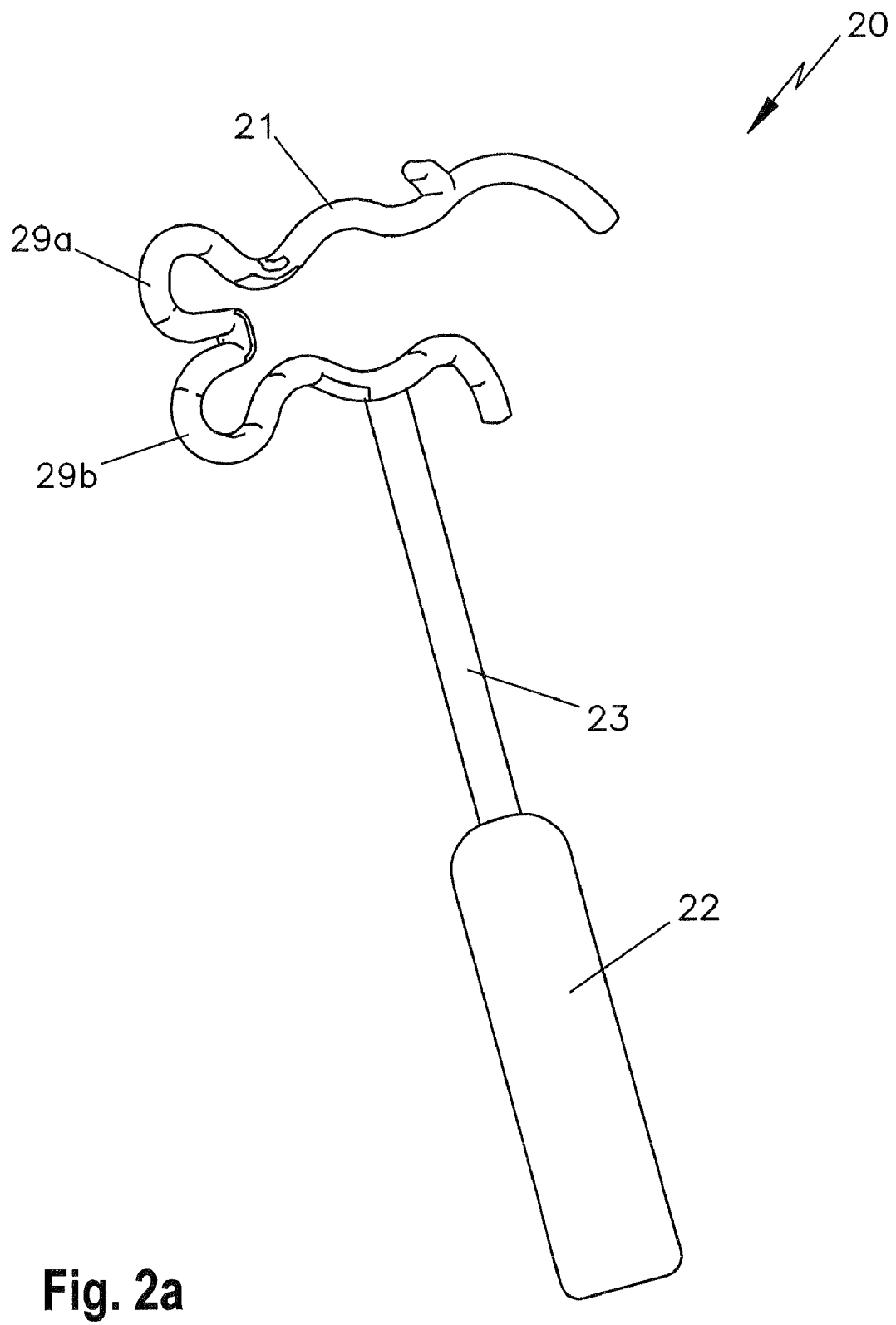
FIG. 2a, a schematic three-dimensional view of a second embodiment, with a single-walled clip as the first securing element.

The ossicle prosthesis 20 shown in FIG. 2a has a single-walled elastic clip 21 on one end, with two recesses 29a, 29b; this clip is in turn joined via an elongated shaft 23 to a piston 22 located on the other end of the prosthesis 20.

Figure 2B:
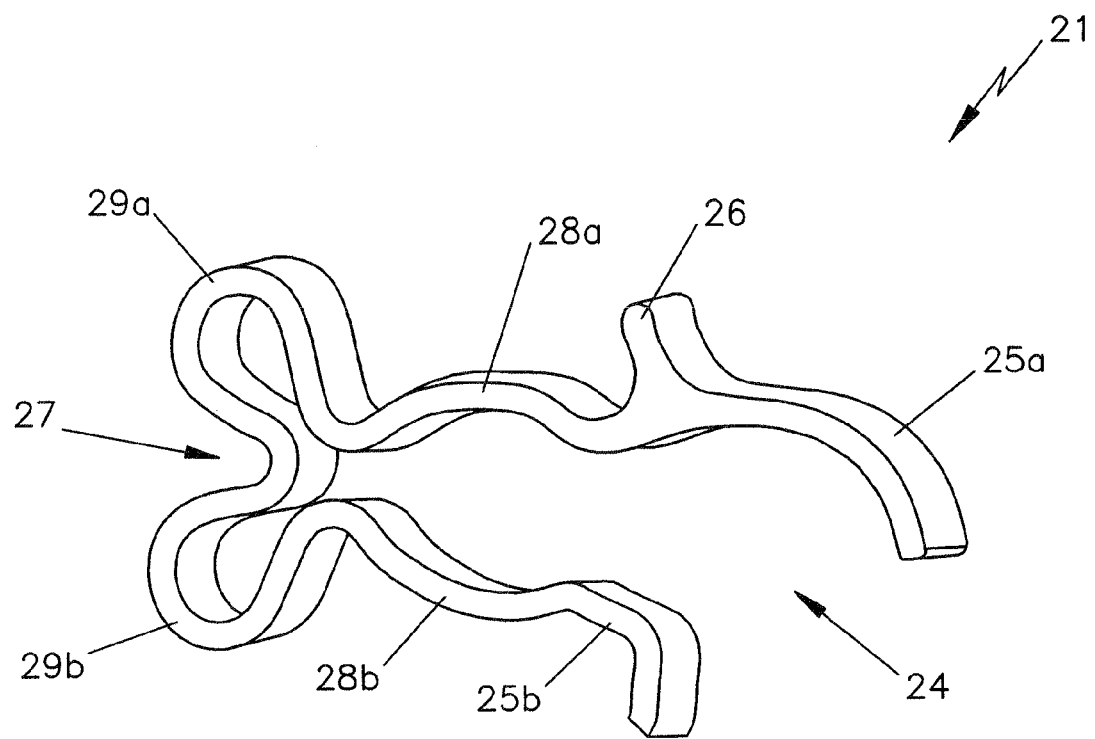
FIG. 2b, the first securing element of the ossicle prosthesis of FIG. 2a in greater detail.

FIG. 2b shows the elastic clip 21 of FIG. 2a in greater detail, with the two circularly outward-curved recesses 29a, 29b for varying the spring characteristic. The clip 21 is again embodied in the form of a clamp open on one side, but in contrast to the embodiment of FIG. 1 it is only single-walled and can be slipped with its outer opening 24 over a member of the ossicle chain, such as the long process of the incus.

In the exemplary embodiment shown, the clamp is lengthened with the upper one of its two legs 25a, 25b outward past its outer opening 24, and this lengthening has the shape of an arc with which, before the clamp is slipped on, the entire prosthesis 20—similarly to what is done in the exemplary embodiment of FIG. 1 by means of the one suspension recess 41—can be suspended from the member of the ossicle chain with which the mechanical connection is to be made, such as the long process of the incus.

To facilitate slipping the prosthesis on, the clamp is provided on its outside with a nipple 26 (and/or with a notch, in embodiments not shown in the drawing), which the surgeon can engage for instance with forceps or a hook. In order to slip the prosthesis 20 onto a member of the ossicle chain, such as the long process of the incus, a surgical instrument can also be positioned in the recess 27 formed between the two recesses 29a, 29b that are curved circularly outward.

After the prosthesis 20 has been slipped on, the clip 21 touches the ossicle in only two diametrically opposed, curved portions 28a and 28b. The rear region of the clip 21 located between them, which has the two recesses 29a, 29b, extends in the implanted state at a relatively great distance from the ossicle, so that the supply vessels to the ossicle cannot become closed off there by the clip 21.

Figure 3:
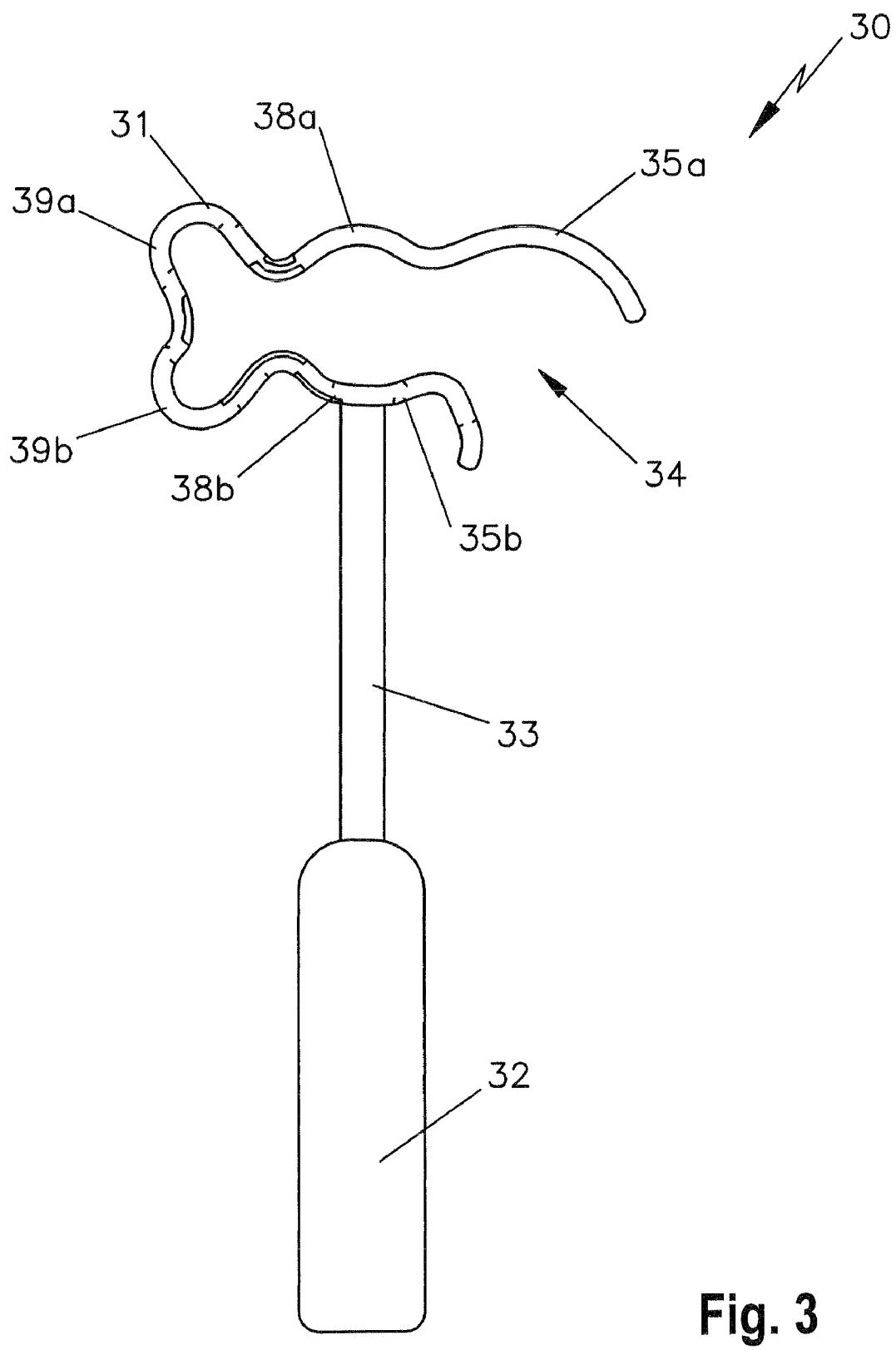
FIG. 3, a schematic three-dimensional view of a third embodiment, in which the first securing element is embodied as in FIG. 2a as a single-walled clip, but with markedly more shallowly curved recesses.

The prosthesis 30 of FIG. 3 has a clip 31, which is shaped quite similarly to the clip 21 of FIGS. 2a and 2b. However, here the two recesses 39a, 39b curved outward in a circular arc are embodied as slightly shallower than in the above-described embodiments of FIGS. 1 through 2b, resulting in a somewhat harder spring characteristic and thus greater stiffness of the clamp.

Otherwise, the clip 31 is embodied similarly to the clip 21 and is again connected in an acoustically hard way, via an elongated shaft 33, to a piston 32 on the other end of the prosthesis 30. Once again, the upper one of the two legs 35a, 35b of the clamp, between which the outer opening 34 is located, has a curved portion, with which the prosthesis 30 can be suspended, for instance from the long process of the incus. Moreover, after being slipped onto the corresponding ossicle, the clip 31 again rests on the bone with only two diametrically opposed, curved portions 38a and 38b, in order to protect the supply vessels located on the outside.

The ossicle prostheses of the invention can differ from one another, among other ways in their length and also in the thickness of the material employed.

On their other end, diametrically opposite the first elastic clip 11; 21; 31, the ossicle prosthesis of the invention, in embodiments not shown in the drawing, can have, instead of the above-described piston 12; 22; 32, a second clip by means of which the respective prosthesis can be joined to a further member of the ossicle chain, such as the stapes.

To gain a certain amount of articulation, embodiments of the invention also not shown in the drawing may have an articulation point or many articulation points engaging one another, which as a rule are located on or in the elongated shaft 13; 23; 33 or replace it.

For additional improvement in hearing quality, in further embodiments not shown in the drawings, a mass may be mounted on the elongated shaft 13; 23; 33, which mass serves the purpose of fine-tuning of the acoustical properties of the ossicle prosthesis by means of purposeful shifting of the resonant frequency to a desired value.

The outer surface of the ossicle prosthesis 10; 20; 30 can furthermore be provided with a biological coating, which inhibits growth or promotes growth as needed. A growth-inhibiting coating is of particular importance, especially in the area where the piston 12; 22; 32 passes through the opening in the base of the stapes, since in this case the prosthesis is seated in the inner ear and is intended to vibrate, so that additional growth at this point must be prevented in every case. Thus the growth-inhibiting coating acts here like a separation layer. The surface of the first elastic clip 11; 21; 31 facing toward the process of the incus can conversely be provided with a growth-promoting coating, not shown in the drawing. The coating may also have germ-killing and in particular antibacterial effects and, after implantation of the prosthesis 10; 20; 30 in the middle ear, can automatically and over a relatively long period of time continuously give off substances, especially antibiotics, to its surroundings.

The invention claimed is:

1. An ossicle prosthesis which is configured to replace or span at least one member of the human ossicle chain, the prosthesis comprising a securing element on at least one end of an elongated shaft for mechanical connection with a member of the ossicle chain; and said securing element has a walled element terminating in opposing ends defining an opening on one side of an elastic clip for receiving the at least one member; and wherein said opposing ends are located diametrically opposite the opening and an opposite side of said clip including a portion of the walled element forming an inwardly curved recess disposed between at least two outwardly curved circular recesses.

2. An ossicle prosthesis as defined in claim 1, wherein said securing element is double-walled and includes a closed outer wall and open inner wall which is open on its side opposite to said opening.

3. An ossicle prosthesis as defined in claim 2, wherein said inner wall has two portions having a shape that is recessed in a direction of said outer wall and forming a receiving region for receiving the member of the ossicle chain.

4. An ossicle prosthesis as defined in claim 3, wherein said inner wall has an additional opening which is adjacent to said outer wall and is spaced from a portion diametrically opposite it with a spacing which is greater than a spacing between said recessed portions of said inner wall and a portion of said outer wall.

5. An ossicle prosthesis as defined in claim 4, wherein said outer wall has an outward-oriented region located adjacent to said additional opening and provided with an element selected from the group consisting of an eye, a nipple, and a recess.

6. An ossicle prosthesis as defined in claim 2, wherein said inner wall in a region of said opening has a suspension recess.

7. An ossicle prosthesis as defined in claim 2, wherein said inner wall in a region of said opening has a lead-in chamfer.

8. An ossicle prosthesis as defined in claim 1, wherein said clamp has at least one leg which is lengthened outward past said opening in form of an arc with which the prosthesis, before the clamp is slipped on, can be suspended from the member of the ossicle chain.

9. An ossicle prosthesis as defined in claim 1, wherein the clamp is provided on its outside with an element selected from the group consisting of a nipple, a notch, and both for slipping the prosthesis onto the member onto the ossicle chain.

10. An ossicle prosthesis as defined in claim 1, wherein said securing element is located on one end of said elongated shaft, and the shaft is configured to connect said securing element to another end of the prosthesis.

11. An ossicle prosthesis as defined in claim 1, wherein the prosthesis has at least in some portions a biologically active coating.

12. An ossicle prosthesis as defined in claim 1, wherein the prosthesis or parts thereof are composed of a metal selected from the group consisting of titanium, steel, tantalum, and an alloy of the aforementioned metals.

13. An ossicle prosthesis as defined in claim 1, wherein said the prosthesis or parts thereof are composed of a material with a shape memory.

14. An ossicle prosthesis as defined in claim 13, wherein the material with the shape memory is Nitinol.

15. An ossicle prosthesis as defined in claim 1, wherein the prosthesis or parts thereof are composed of a biocompatible plastics.

16. An ossicle prosthesis as defined in claim 1, wherein individual parts of the prosthesis are configured so that a mass distribution of the individual parts of the prosthesis is calculated as a function of the desired, predeterminable frequency response of a conduction of sound in a middle ear.

17. An ossicle prosthesis as defined in claim 1, wherein the prosthesis is configured to couple directly to an inner ear by opening a human cochlea with other end of said elongated shaft.

18. An ossicle prosthesis as defined in claim 17, wherein the ossicle prosthesis is configured to couple directly to the inner ear via a piston.

19. An ossicle prosthesis as defined in claim 1; and further comprising a further securing element located on another end of the prosthesis, placed counter to said clip, for mechanical connection to a further member to the ossicle chain.

20. An ossicle prosthesis as defined in claim 19, wherein said further securing element is double-walled.

\* \* \* \* \*